United States Patent [19]

Hee

[11] Patent Number: 5,004,425

[45] Date of Patent: Apr. 2, 1991

[54] MAGNETIC SNAP ASSEMBLY FOR CONNECTING GROUNDING CORD TO ELECTRICALLY CONDUCTIVE BODY BAND

[75] Inventor: Roland Hee, Manilla, Philippines

[73] Assignee: JES, L.P., Carlsbad, Calif.

[21] Appl. No.: 419,409

[22] Filed: Oct. 10, 1989

[51] Int. Cl.$^5$ .............................................. H01R 4/66
[52] U.S. Cl. .................................... 439/37; 439/39; 439/92; 361/220
[58] Field of Search .................. 439/37, 39, 38, 92; 361/212, 220

[56] References Cited

U.S. PATENT DOCUMENTS

| | | | |
|---|---|---|---|
| 1,531,862 | 3/1925 | Larned | 273/730 |
| 2,928,100 | 3/1960 | Gagnon | 2/339 |
| 2,998,697 | 9/1961 | Augenstein | 59/80 |
| 3,063,447 | 11/1962 | Kirsten | 128/134 |
| 3,377,509 | 4/1968 | Legge | 317/2 |
| 3,422,460 | 1/1969 | Burke et al. | 2/73 |
| 3,424,698 | 1/1969 | Lupinski et al. | 252/500 |
| 3,459,997 | 8/1969 | Legge | 317/2 |
| 3,541,389 | 11/1970 | Van Name | 317/2 |
| 3,582,448 | 6/1971 | Okuhashi et al. | 161/87 |
| 3,596,134 | 7/1971 | Burke | 317/2 B |
| 3,699,590 | 10/1972 | Webber et al. | 2/73 |
| 3,810,258 | 5/1974 | Mathauser | 439/39 |
| 3,812,861 | 5/1974 | Peters | 128/418 |
| 3,832,841 | 9/1974 | Cole | 57/152 |
| 3,851,456 | 12/1974 | Hamada et al. | 57/140 |
| 3,857,397 | 12/1974 | Brosseau | 128/384 |
| 3,904,929 | 9/1975 | Kanaya et al. | 317/2 |
| 3,949,129 | 4/1976 | Hubbard | 428/190 |
| 3,986,530 | 10/1976 | Maekawa | 139/425 |
| 3,987,613 | 10/1976 | Woods et al. | 57/140 |
| 4,025,964 | 5/1977 | Owens | 439/39 |
| 4,112,941 | 9/1978 | Larimore | 439/39 |
| 4,211,456 | 7/1980 | Sears | 439/39 |
| 4,267,233 | 5/1981 | Tanaka et al. | 428/389 |
| 4,321,789 | 3/1982 | Dammann et al. | 57/224 |
| 4,373,175 | 2/1983 | Mykkanen | 361/220 |
| 4,398,277 | 8/1983 | Christiansen et al. | 361/220 |
| 4,402,560 | 9/1983 | Swainbank | 339/11 |
| 4,420,529 | 12/1983 | Westhead | 428/244 |
| 4,422,483 | 12/1983 | Zins | 139/420 |
| 4,453,294 | 6/1984 | Tamso Morita | 24/303 |
| 4,475,141 | 10/1984 | Antonevich | 361/220 |
| 4,577,256 | 3/1986 | Breidegam | 361/220 |
| 4,639,825 | 10/1987 | Breidegam | 361/212 |
| 4,676,561 | 6/1987 | Barrett, II | 439/37 |

FOREIGN PATENT DOCUMENTS

| | | |
|---|---|---|
| 2547390 | 5/1977 | Fed. Rep. of Germany . |
| 3622948 | 1/1988 | Fed. Rep. of Germany ........ 439/39 |
| 1067260 | 5/1967 | United Kingdom . |

OTHER PUBLICATIONS

"Magnetic Ground Strap Connector", AT&T Technical Digest, No. 76, Mar. 1985, pp. 21.

Primary Examiner—Gary F. Paumen
Attorney, Agent, or Firm—Stetina and Brunda

[57] ABSTRACT

A magnetic connection assembly for releasably connecting a ground cord to an electrically conductive body band. Said assembly comprising a first connection member electrically connected to one end of a ground cord and a second connection member electrically connected to a body band. The first and second connection members are at least partially formed of electrically conductive material and are correspondingly sized and configured so as to be relatively positionable in a "coupled" relation, whereby electrical contact is maintained therebetween. At least one magnet is positioned in at least one of the first and second connection members so as to create sufficient magnetic attraction therebetween to hold the first and second connection members in their "coupled" relation without the need for frictional or spring loaded snaps and the like.

5 Claims, 1 Drawing Sheet

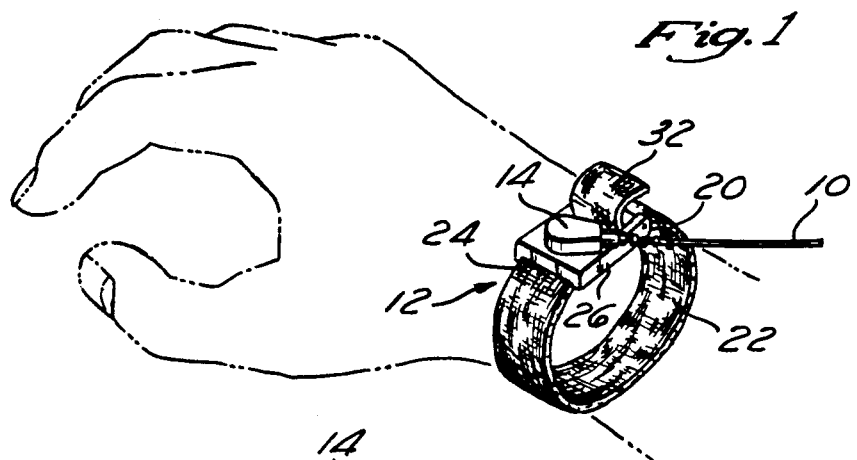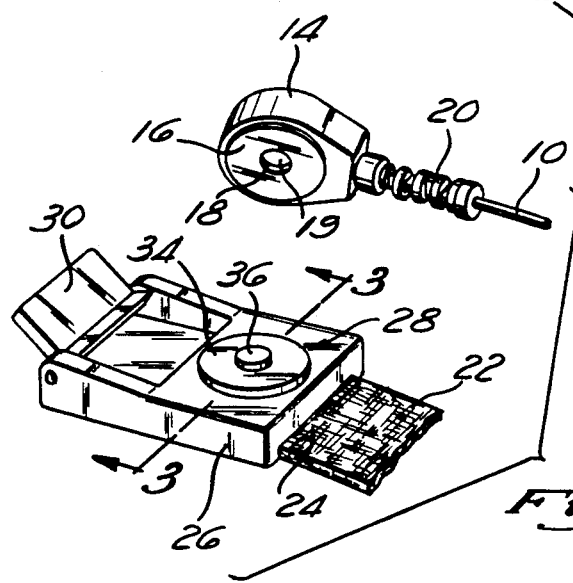

MAGNETIC SNAP ASSEMBLY FOR CONNECTING GROUNDING CORD TO ELECTRICALLY CONDUCTIVE BODY BAND

FIELD OF THE INVENTION

BACKGROUND OF THE INVENTION

The present invention relates generally to electrically conductive body bands (e.g., wrist bands, ankle bands, and the like) used to drain static electricity from the human body. More particularly, this invention pertains to an improved magnetic snap assembly for releasably connecting a grounding cord to an electrically conductive body band.

The routine handling of static-sensitive electronic components is plagued by problems relating to static electricity. Components, such as integrated circuits, for example, are prone to serious damage due to over-voltage or excessive power density resulting from static electricity. Static electrical potentials of as little as 50 vots may seriously damage certain integrated circuits and/or other microelectronic components. This potential for static electricity-induced damage is significant in view of the fact that static electrical potentials of as much as 30,000 volts may be generated by a person moving about on a carpet in a generally dry atmosphere. Also, human beings may triboelectrically generate thousands of volts of static potential by simply changing position in a chair or handling a styrofoam cup.

In order to minimize or avoid static electric-induced damage to electrical components, it is common practice in the electrical component manufacturing industry to attach grounding cords to the workers so as to drain static electricity from the bodies of the workers when they are handling such components. Generally, this is accomplished by placing an electrically conductive body band (e.g. a wrist band, ankle band, or the like) about an anatomical portion of the person's body. Such body band is then connected to a grounding cord so as to effect the desired wicking or drainage of static electricity from the body. The connection between body band and the grounding cord is preferably of an easy-release type so as to allow the worker to easily disconnect himself from the grounding cord when he wishes to ambulate away from the work area.

To date, the connecting means employed for releasably attaching the grounding cord to the body band have consisted of spring loaded and/or frictionally engaged straps. Such snaps generally provide for easily attachable/detachable, electrically conductive interconnections. However, in some instances, the spring-loaded and/or frictionally engaged snaps haVe failed to function reliably, thereby resulting in inefficient or interrupted draining of static electricity from the body of the user. Oftentimes, the failure of the spring-loaded and/or frictionally engaged snaps has been.due to improper fitting and/or incompatible configurations of the male and/or female portions thereof. Such improper fitting or incompatible configurations are likely to occur when the snaps become damaged, bent, worn, or fouled with dirt/foreign objects. Also, unsophisticated users may sometimes attempt to mate a grounding cord from one manufacturer with a body band from another manufacturer, ignoring the fact that the male snap portion on one may be configured quite differently than the female snap portion on the other. The union so such unpaired snap portions may result in ineffective contact and disrupted electrical conductivity therebetween.

Thus, in view of the problems associated with frictional or spring loaded snap connections, there remains a need in the art for an improved connector for releasably connecting a grounding cord to a body band in such manner as to permit rapid and simple disconnection/reconnection while, at the same time, insuring adequate electrical conductivity and consistency to carry out the desired static electricity Wicking function.

SUMMARY OF THE INVENTION

The present invention overcomes some or all of the shortcomings of the prior art by providing a magnetic connection assembly for releasably connecting a ground cord to an electrically conductive body band, such as a wrist band, ankle band or the like. The magnet connections assembly of the invention comprises a first connection member electrically connected to one end of a ground cord and a second connection member electrically connected to the body band. The first and second connection members are at least partially formed of electrically conductive material and are correspondingly sized and configured so as to be relatively positionable in "coupled" relation, Whereby electrical contact is maintained therebetween. At least a portion of at least one of the first and second connection members is magnetized. Also, at least a portion of the other of said first and second connection members is formed of ferromagnetic material so that there exists sufficient magnetic attraction between the first and second connection members to hold them in their "coupled" relation.

One of the first and second connection members is formed a male connector, while the other if formed as a female connector. The male connector registers or slidably inserts within the female connector so as to position and align the connection members when they are in their "coupled" positions. Generally, the male and female connection members are formed so as to fit together without undue pressure, friction, or the need for dilating spring members or the like.

Magnetically conductive flanges are formed around the male and female portions of the connection members, so that when the connection members are placed in their "coupled" positions, these symmetrically conductive flanges will abut one another, thereby enhancing the electrical contact formed between the first and second connection members.

In embodiments where the magnetic connection assembly of the present invention is used in connection with an elastic fabric body band, one of the connection members is attached to the body band by way of an attachment assembly comprising a rigid body upon which the connection member is mounted and through which one end of the flexible body band is past. An electrically conductive plate is mounted on the underside of the rigid body and a rivet or other member is passed upwardly therethrough so as to secure the connection member upon the rigid body and in contact with the electrically conductive body band. By such arrangement, the electrically conductive plate positioned on the underside of the rigid member enhances transmission of the electricity from the electrically conductive body band to the connection member mounted thereon.

BRIEF DESCRIPTION OF THE DRAWINGS

FIG. 1 is a perspective view showing a preferred magnetic connector of the present invention operatively connecting a grounding cord to an electrically conductive wrist band;

FIG. 2 is an exploded view showing the opposite portions of a preferred magnetic connector of the present invention;

FIG. 3 is a cross-sectional view through line 3—3 of FIG. 2;

FIG. 4 is an exploded view of the opposite portions of the core of a magnetic connector of the present invention; and FIG. 5 is an enlarged perspective view of portions of an anti-static wrist band and an attendant grounding cord incorporating a magnetic connection assembly in accordance with the present invention.

DETAILED DESCRIPTION OF THE PREFERRED EMBODIMENT

The following detailed description and the accompanying drawings are provided for purposes of describing and illustrating one presently preferred embodiment of the invention. This detailed description and the accompanying drawings are not intended to limit the scope of the invention in any way.

Referring to the drawings, a preferred magnetic snap assembly of the present invention is employed to connect a grounding cord 10 to an anti-static Wrist band 12 or other type of body band.

A female connection member 14 is positioned on the distal end of the grounding cord 10. Such female connection member 14 comprises a metal disk-like body substantially in the form of a female connector. Such female connector 14 comprises a generally flat, circular metal surface 16 with a recessed notch 18 having a magnet 19 positioned in the center thereof. Such first magnetic connection member 14 is electrically connected to the grounding cord 10 so that the circular metal surface 16, notch 18 and magnet 19 are sufficiently grounded to serve as contact surfaces for wicking or removal of static electricity from the Wrist band 12 When appropriately connected to the opposite male connector 28 located on the wristband.

A bendable plastic sleeve 20 is formed around the distal portion of the grounding cord 10, adjacent its connection to the first magnetic connection member 14. Such sleeve 20 provides for resilient bending of the distal-most portion of the cord 10 without undue wear and/or crimping of the cord 10.

Many types of anti-static body bands (e.g. Wrist bands, ankle bands, torso bands, etc. . . ) may be employed in connection with this invention. However, the particular embodiment shown in the drawings is a flexible wrist band comprising an elastic fabric strip 22 having electrically conductive yarns disposed on the inner surface thereof. A first end 24 of the elastic fabric strip 22 is permanently affixed within a generally rectangular rigid body 26. The male connection member 28 of the present invention is mounted or formed within the rectangular rigid body 26 so as to provide for convenient mating of the female 14 and male 2B connection members to achieve the desired electrical grounding.

A clasp member 30 is also formed on the opposite side of the generally rectangular body 26 and serves to hold the second end 32 of the fabric strap in place and also provides for adjustability of the length of the strap 22, insuring its snug fit around the wrist or other anatomical portion of the body.

The male connection member 28 mounted upon the rectangular body comprises a generally flat metal circular flange 34 having a lug or raised disk 36 extending upwardly from the center thereof. The raised disk 36 is sized and configured to slidably insert into the female notch 18 of the female connecting member 14 in the manner shown in FIG. 5.

The metal surfaces of the raised disk 36 and the flange 34 are subject to magnetic attraction by magnet 18. Thus, when the female connector 14 is placed in juxtaposition with the male connector 28, the magnetic field emanating from the magnet 18 will pull the male 28 and female 14 connection members into direct abutting contact. By such arrangement the electrically conductive surfaces of the flanges 34, 16 and/or the lug 36 and notch 19 are held in firm, continuous electrical contact.

The manner in which the elastic fabric strap 22, rectangular body 26, and male connection member 28 are assembled is specifically shown in FIGS. 3 and 4. As shown, the first end 24 of the elastic fabric strap 22 is inserted within the rectangular body 26. An aperture 38 is formed in the upper surface of the rectangular body 26. A cylindrical shaft 40 extends doWnWardly from the body of the male connection member 28. Such cylindrical shaft 40 is inserted downwardly through aperture 38 and through a small hole formed in the fabric of strap 22. A metal bottom plate 42 or cover is then positioned over the underside of the rectangular body 26. The metal bottom plate 42 is provided with a depressed or indented central region having a central aperture formed therein. Also, the lateral edges of the metal bottom plate 42 upturned to form side lip members 44, 46 which pass slidably inboard of the downturned outer edges of the rectangular body 26. After the bottom plate 42 has been placed in position, a rivet 46 is advanced upwardly through the central aperture of the bottom plate, through the hole formed in the elastic fabric strap 22, and is advanced onto the cylindrical shaft 40 of the male connection member 28. The rivet 46 is pressed upwardly so that shaft 40 is received within the inner bore 48 of rivet 46. The rivet is then creased or crimped around shaft 40 so as to hold the bottom plate 42 in its fully upwardly advanced position wherein the top edges of lips 44, 46 abut directly against the roof Of the rectangular body 26 such that the bottom plate 42 will compress the fabric of the wristband 22. By such arrangement, the fabric wristband 22 is compressed between the bottom plate 42 and the inner surface of the rectangular body 26 in such a manner that direct contact is maintained between the electrically conductive threads present on the lower surface 50 of the fabric strap 22 and the upper surface 52 of the metal bottom plate 42. Such contact between, the electrically conductive threads formed in the fabric strap 22 and the metal bottom plate 42 results in electrical connection and conduction from the skin of the wearer, through the bottom plate 42 and/or rivet 46, and into the male connection member 28.

When the female connection member 14 is placed on top of the male connection member 28, electrical contact is formed therebetween so that static electricity may be drained from the wrist band 12 through the grounding cord 10, thereby effecting the desired antistatic function.

Although the invention has been described herein with reference to the presently preferred embodiment shown in the drawings, it Will be appreciated that various other embodiments are contemplated and that numerous additions, modifications, and alterations may be made to the embodiment shoWn. For example, the male and female connection members may be configured in many differed ways and are not limited to a single configuration wherein a single lug 36 fits into a single notch 18 as shown in the drawings. Indeed, a plurality of lugs, annular ridges or other members may be formed on the male portion and the female portion may be correspondingly configured so that the plural lugs, ridges etc., of the male portion will register therewithin, so as to locate and position the connection members for optional electrical contact therebetween. Also, magnet(s) may be located on either or both (e.g. male and female) portions of the connector. In embodiments where two magnets are employed, the magnets will be mounted so that opposite magnetic poles will juxtapose when the connection members are placed in their "coupled" positions. Accordingly, it is intended that any and all such additional embodiments, additions, modifications. and alterations be encompassed within the scope of the following claims and the equivalents thereof.

What is claimed is:

1. An antistatic body band and ground cord assembly for conducting static electricity away from the wearer's skin, the assembly comprising:
   (a) a body having an upper surface and a lower surface, the lower surface having a recess formed therein;
   (b) a conductive bottom plate disposed partially within the recess of said body and having an aperture formed therein;
   (c) an elastic strip having first and second ends and having conductive fibers woven therein, the first end of said strap having an aperture formed therein and being captured intermediate said bottom plate and said body, the second end of said strap being attachable to said body;
   (d) a ferromagnetic flange disposed upon the upper surface of said body, said flange having a generally planer upper surface, a raised ferromagnetic lug formed upon the upper surface, and a conductive shaft formed upon the lower surface of said flange, the shaft extending downward through said body;
   (e) a rivet extending through the aperture formed in said bottom plate and through the aperture formed in said elastic strip, said rivet being attached to the shaft o said flange;
   (f) a magnetic connection member having a substantially planar lower surface and a recess formed within the lower surface such that said connection member may couple with said flange, said lug being received within said recess;
   (g) a conductive ground cord attached at one end to said connection member;
   (h) wherein said magnetic connection member releasably attaches said ground cord to said flange and provides electrical conduction therebetween; and
   (i) wherein said bottom plate, said rivet, said shaft, and said flange cooperate to provide electrical conduction from said elastic strap and from the wearer's skin to said magnetic connection member, and also cooperate to attach themselves and said body and the first end of said elastic strap together.

2. The antistatic body band and ground cord assembly as recited in claim 1 wherein the second end of said strap is adjustably attached to said body.

3. The antistatic body band and ground cord assembly as recited in claim 2 further comprising a clasp member disposed upon said body for adjustably attaching the second end of said strap to said body.

4. The antistatic body band and around cord assembly as recited in claim 3 wherein said bottom plate further comprises two unturned lip members, said lip members providing a tight fit between said bottom plate and the recess formed within said body to prevent rotation of said bottom plate.

5. The antistatic body band and ground cord assembly as recited in claim 4 wherein said bottom plate further comprises a recess formed to receive said rivet such that no part of said rivet extends beyond the lower surface of said bottom plate, the upper surface of said recess contacting the first end of said strap.

* * * * *